(12) United States Patent
Kato et al.

(10) Patent No.: US 10,139,390 B2
(45) Date of Patent: Nov. 27, 2018

(54) ANALYSIS DEVICE

(71) Applicant: HITACHI HIGH-TECHNOLOGIES CORPORATION, Tokyo (JP)

(72) Inventors: Hirokazu Kato, Tokyo (JP); Tomohiro Shoji, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 232 days.

(21) Appl. No.: 14/898,298

(22) PCT Filed: Apr. 18, 2014

(86) PCT No.: PCT/JP2014/061000
§ 371 (c)(1),
(2) Date: Dec. 14, 2015

(87) PCT Pub. No.: WO2014/208184
PCT Pub. Date: Dec. 31, 2014

(65) Prior Publication Data
US 2016/0153960 A1    Jun. 2, 2016

(30) Foreign Application Priority Data

Jun. 28, 2013 (JP) .................................. 2013-135739

(51) Int. Cl.
*G01N 33/487* (2006.01)
*C12Q 1/6869* (2018.01)
*G01N 27/447* (2006.01)

(52) U.S. Cl.
CPC ..... *G01N 33/48721* (2013.01); *C12Q 1/6869* (2013.01); *G01N 27/44791* (2013.01)

(58) Field of Classification Search
CPC . B81B 3/0018–3/0032; B81B 3/0035–3/0059; G01N 27/3278; C12Q 2565/631
See application file for complete search history.

(56) References Cited

U.S. PATENT DOCUMENTS 8,039,250 B2    10/2011 Peng et al.
2007/0298511 A1*  12/2007 Kang ............... C01N 33/48721
                                                          436/150
(Continued)

FOREIGN PATENT DOCUMENTS

EP         2755022     *  1/2013   ....... G01N 33/48721
WO     WO 2013011879   *  7/2011   ....... G01N 33/48721

OTHER PUBLICATIONS

He et al. (Nano Letters, 2012, 7/1, 538-546).*
(Continued)

*Primary Examiner* — Gurpreet Kaur
*Assistant Examiner* — Steven E Rosenwald
(74) *Attorney, Agent, or Firm* — Mattingly & Malur, PC

(57) ABSTRACT

By slowing down the passing velocity of a DNA molecule in a nanopore, the accuracy of the reading of a nucleotide sequence of DNA is improved. A small temperature difference is introduced between a DNA molecule having an asymmetric and periodic structure and a nanopore membrane that carries the DNA molecule, whereby the DNA molecule that passes through a nanopore can move in one direction and the passing velocity of the DNA molecule in the nanopore can be controlled and reduced. In this manner, the accuracy of the analysis of a nucleotide sequence can be improved. Furthermore, it becomes possible to dissociate double-stranded DNA into single-stranded DNA molecules by the action of temperature and subject the single-stranded DNA molecules to a measurement selectively. Furthermore, it also becomes possible to select the polarity of a DNA molecule and subject the DNA molecule to a measurement.

18 Claims, 10 Drawing Sheets

(56) References Cited

U.S. PATENT DOCUMENTS

| | | | |
|---|---|---|---|
| 2010/0146991 A1* | 6/2010 | Ilercil | F25B 21/02 |
| | | | 62/3.5 |
| 2010/0327255 A1 | 12/2010 | Peng et al. | |
| 2012/0193235 A1 | 8/2012 | Afzali-Ardakani et al. | |
| 2013/0186758 A1* | 7/2013 | Saha | G01N 27/44791 |
| | | | 204/452 |

OTHER PUBLICATIONS

Garaj et al. (Nature 467/9, Sep. 9, 2010).*
Postma (Nano Letters, 2010, 10, 42-425).*
Eslami-Mossallam, B. et al., "An Asymmetric Elastic Rod Model for DNA", Department of Physics, Sharif University of Technology, Apr. 26, 2009, pp. 1-5, Iran.
Feynman, R. P. et al. "Rachet and Pawl", The Feynman Lectures on Physics: Mainly Mechanics, Radiation, and Heat, Chapter 46 pp. 46-1-46-9, vol. 1.
International Search Report of PCT/JP2014/061000.
Bala Murali Venkatesan et la., "Nanopore sensors for nucleic acid analysis", Nature Nanotechnology, Oct. 2011, pp. 615-624, vol. 6., Published online Sep. 18, 2011, www.nature.com/naturenanotechnology.
Daniel Fologea et al., "Slowing DNA Translocation in a Solid-State Nanopore" Nano Letters, 2005, pp. 1734-1737, vol. 5, No. 9.
Makusu Tsutsui et al., "Single-molecule sensing electrode embedded in-plane nanopore", Scientific Reports, Jul. 28, 2011, pp. 1-6.
S. Garaj et al., Graphene as a subnanometre trans-electrode membrane, Nature Letters, Sep. 9, 2011, vol. 467.

* cited by examiner a)

b)

ANALYSIS DEVICE

TECHNICAL FIELD

The present invention relates to an analysis device. More specifically, the present invention relates to a method for decoding a base sequence of a nucleic acid such as DNA or RNA and a nucleic acid sequence analysis device.

BACKGROUND ART

Development of a nanopore technology has been performed popularly. "Advanced Sequencing Technology Awards" which started to be granted by NHGRI (National Human Genome Research Institute, U.S.A.) in 2004 by using decoding the human genome in 2003 as a meter, was established in order to recommend technological development of a next-generation sequencer. The largest investment of these grants is the nanopore technology. The nanopore technology occupies 29 of 60 projects to which funds were granted from 2004 to 2010.

The nanopore includes bionanopore and solid nanopore. The bionanopore treats protein and a lipid bilayer which are biomolecules. These substances are easily denatured disadvantageously. When measurement is performed with the bionanopore, it is necessary to supply protein and the lipid bilayer to a flow cell before the measurement, and workability is poor. Therefore, expectation for the solid nanopore which does not have to treat these biomolecules has been increased.

One of big problems of the solid nanopore technology is that a passing speed of a DNA molecule passing through the nanopore is too high. In the present circumstances, the speed of DNA passing through the solid nanopore is 100 µm/s (=3 µs/base). It is necessary to reduce the passing speed to 0.3 µm/s (=1 ms/base) in order to detect a base sequence with resolution of one base. This problem is reported in detail in NPL 1.

As a method for reducing the passing speed of DNA, in NPL 2, a method for adjusting the temperature, pH, viscosity, or the like of a solution, is examined. Fologea et al. have succeeded in reducing the passing speed of a DNA molecule from 0.3 m/s to 1 mm/s by optimizing these conditions. However, 1 mm/s is higher than 0.3 µm/s as an ideal speed by about four orders of magnitude, and it is necessary to further reduce the passing speed. It is recognized that a signal of a blockage current used for detecting a DNA base is also reduced disadvantageously with the increase of the passing speed.

PTL 1 proposes a nanopore film having a film structure in which a plurality of conductive films and insulating films are stacked on each other. It is described that the passing speed of a DNA molecule passing through a nanopore can be controlled by using this nanopore film. A cylindrical piezoelectric element is embedded in a nanopore opening. The piezoelectric element is in contact with the conductive film to be energized. The piezoelectric element can be extended or compressed by a nanometer scale according to a voltage applied thereto. A DNA molecule in a solution is guided to the nanopore opening by an electrode disposed in a flow cell, invades the nanopore opening, and starts to pass through the nanopore. The time when the DNA molecule starts to pass through the nanopore can be specified by detecting decrease in a blockage current. At the same time as the time when the DNA molecule starts to pass through the nanopore, a voltage is applied to the piezoelectric element embedded in the nanopore opening, and the piezoelectric element is expanded. The DNA molecule in the nanopore can be thereby captured. It is possible to control the passing speed of the DNA molecule in the nanopore by controlling a potential with respect to the piezoelectric element in a pulse while an external electric field is applied to the DNA molecule. Alternatively, it is described that each base of the DNA molecule can go unidirectionally in the nanopore.

PTL 2 proposes a nanopore structure in which a gate electrode film is sandwiched by insulating films and the outside thereof is further sandwiched by a source electrode film and a drain electrode film. This patent literature is also for controlling a passing speed of a DNA molecule in a nanopore. It is possible to control an orientation of ions in a solution including an electrolyte in the nanopore by further applying a gate voltage while a constant voltage is applied between the source and drain electrode films in advance. For example, it is possible to form a (negative, positive, negative) ion layer in the nanopore while the gate voltage is applied. On the other hand, it is possible to form a (negative, negative, negative) ion layer in the nanopore while the gate voltage is not applied. In the former state, flows of the ions are blocked in two regions separated by a nanopore film. However, in the latter state, the ions can flow in. This means that an ion current in an aqueous solution can be controlled. MOS-FET which is popular in a digital camera or the like controls an electronic circuit by turning on or off a flow of electrons. Similarly to this, a flow of ions in the aqueous solution can be controlled in this patent literature. In this patent literature, this idea is named "nano fluidic FET." The DNA molecule and the ions are charged. In a broad sense, motion of DNA in the nanopore can be regarded as a flow of ions. Therefore, it is possible to control the passing speed of the DNA molecule in the nanopore using the "nano fluidic FET".

In PTL 3, a nanopore film is produced using an insulating film. An organic molecule is modified to a nanopore opening in contact with DNA. A weak and transitional bond (for example, hydrogen bond) is formed between this organic molecule and the DNA molecule. This bond is stronger than thermal fluctuation of the DNA molecule, and therefore the DNA molecule can be captured in the nanopore. It is described that a passing speed of DNA can be controlled by applying a voltage to the DNA molecule in a pulse in vertical upper and lower directions of the nanopore film.

In conventional nanopore measurement, a phenomenon in which an ion current is reduced when the DNA molecule passes through the nanopore, that is, a blockage current is measured. However, the blockage current is extremely feeble, and parallelization is difficult. Therefore, a method in which a microelectrode is disposed on the nanopore film and a tunneling current generated when the DNA passes is measured, is becoming the mainstream. In NPL 3, it was confirmed that monomers A, T, G, C, and U had electric conductivities different from each other in measurement of a tunneling current using a microelectrode. Thereafter, it was tried to discriminate one base in a three base DNA (GGG, GTG, TGT, or the like) and a seven base RNA (UGA GGU A, apart of cancer marker let-7 miRNA sequence). In the change of the current with time, a step-shaped change for each base was observed. However, the change was not observed in the order of the sequence, but some parts of the sequence, such as GGTG or TG, were repeated or missed. This is because the moving direction of the DNA molecule cannot be controlled and the DNA molecule moves at random by an irregular Brownian motion. When only the step-shaped change of a current was extracted and all the data points converted into the electric conductivity were made into a histogram, a distribution having two peaks was observed. A value of the electric conductivity of the peak value was the same as a value obtained by the monomer. It was also possible to measure the change of the electric conductivity for each base of the seven base RNA. It was found that the seven base sequence could be determined by arranging the above-described measurement sequences in a large amount like a shotgun sequence and performing statistical processing.

Meanwhile, it is a thermal ratchet mode that has attracted attention as a method for moving a substance unidirectionally in a micro region. This model includes a ratchet having asymmetric teeth, an impeller, and a clasp on the wall. This impeller is in a gas at a temperature T1. Therefore, a gas molecule collides with the impeller, and the impeller receives a random force clockwise or counterclockwise. The temperature of the clasp is represented by T2. A spring is attached to the clasp. When the ratchet tries to rotate clockwise, the clasp retracts to the left side and the ratchet can rotate. When the ratchet tries to rotate counterclockwise, the ratchet stops at the clasp. In this system, it is known that unidirectional rotation does not occur as long as there is no temperature difference between the temperature T1 of the impeller and the temperature T2 of the spring. In other words, it is known in principle that unidirectional motion is caused if a temperature difference between T1 and T2 can be introduced. NPL 4 describes this technology.

A single stranded DNA molecule is a polymer obtained by polymerizing molecules dATP, dCTP, dGTP, and dTTP which are asymmetric and have very similar structures. Therefore, the single strand DNA molecule has a spiral shape, and an asymmetric shape and a potential for each base on an axis thereof. Conventionally, an elastic rod model which assumes symmetry of a molecule has been employed for rigidity of the DNA molecule. However, experimental results in which the rigidity of the DNA molecule cannot be explained with this model have been submitted recently. In order to explain this, NPL 5 describes the rigidity of the DNA molecule with an asymmetric elastic rod model which assumes asymmetry of the DNA molecule.

As a material of the nanopore, graphene has attracted attention recently. Graphene is obtained by extending a hexagonal frame formed by carbon into a sheet-shape. Graphene is obtained by extracting one atomic surface of a graphite crystal. At present, measurement of a blockage current is employed most often in reading a base of DNA in the nanopore. When DNA passes through a nanopore, an effective area of the nanopore through which ions can pass changes. Therefore, a current flowing in upper and lower spaces of the nanopore also changes. This changing current is referred to as the blockage current. This blockage current is measured, and discrimination of four bases included in DNA is performed. However, when a film of the nanopore is too thick, several nucleotide molecules are contained in the film thickness. Therefore, as a result, it is difficult to correspond a base sequence for each base in the DNA molecule to the measured blockage current. A distance between the nucleotides in the DNA molecule is from 0.32 to 0.52 nm. It is necessary to introduce a film having a thickness almost the same as this distance in order to discriminate the base sequence of a DNA molecule passing through the nanopore. Graphene is a useful material to solve this problem. NPL 6 reports that resolution of graphene having a thickness of 0.6 nm for discriminating the DNA base is 0.35 nm in computer simulation. NPL 7 reports excellent physical properties of graphene. The thermal conductivity of graphene is highest in the currently known substances, and is 5000 [W/m/K]. On the other hand, the thermal conductivity of water is 0.6. There is a difference of about four orders of magnitude as the order of thermal conductivity. The Young's modulus of graphene is highest in the currently known substances, and is 1500 [GPa].

CITATION LIST

Patent Literatures

PTL 1: United States patent (pub no: U.S. Pat. No. 8,039,250 B2, Peng et al.)
PTL 2: United States patent application Publication (pub no: US 2010/0327255 A1, Peng et al.)
PTL 3: United States patent application Publication (pub no: US 2012/0193235 A1, Afzali-Ardakani et al.)

Non-Patent Literatures

NPL 1: Nature nanotechnologies, 2011 Sep. 18; 6(10): 615-24
NPL 2: Nano letters, Vol. 5, No. 9, 2005
NPL 3: Scientific Reports, 2012; 2:501. doi: 10.1038/srep00501
NPL 4: The Feynman Lectures on Physics, Volume II, written by Feynman, Leighton, and Sands, translated by Kotaro Tomiyama, issued by Iwanami Syoten, 1986
NPL 5: Phys. Rev. E 80, 011919 (2009)
NPL 6: Nature. 2010 Sep. 9; 467(7312): 190-3
NPL 7: Science & Technology Trends, p. 29-42, May 2010

SUMMARY OF INVENTION

Technical Problem

An object is to improve accuracy of reading a DNA base sequence by lowering a passing speed of a DNA molecule in a nanopore (micropore in the order of nanometer). One of big problems of the nanopore technology is that the passing speed of the DNA molecule passing through the nanopore is too high. In the present circumstances, the passing speed is 300 μm/s (=1 μs/base), and it is difficult to discriminate each base. The object is to lower the passing speed to 0.3 μm/s (=1 ms/base) to be able to determine four bases in DNA.

Solution to Problem

By introducing a very small temperature difference between a DNA molecule having an asymmetric and periodic structure and a nanopore film holding the DNA molecule, the DNA passing through the nanopore (micropore in the order of nanometer) is moved unidirectionally, and a passing speed in the nanopore is controlled.

The DNA molecule is a polymer obtained by polymerizing four kinds of nucleotides having very similar structures. Therefore, this structure has a periodic and asymmetric potential. A temperature difference is introduced between the DNA molecule having an asymmetric potential and a nanopore substrate through which the DNA molecule passes. A pawl in a molecular level is introduced into a nanopore opening. This pawl presses the DNA molecule with a spring, and holds the DNA molecule in the nanopore. By these mechanisms, the DNA molecule performing thermal motion in the nanopore can be driven unidirectionally.

More specifically, the DNA molecule in a solution holds the temperature in the liquid (temperature T1), and the nanopore substrate is cooled to the temperature T2. Here, T1>T2.

Advantageous Effects of Invention

By using the present method, the passing speed of a DNA molecule in a nanopore can be controlled and can be lowered. This can improve accuracy of analyzing a base sequence. A double stranded DNA is unwound into a single stranded DNA according to the temperature, and the single stranded DNA can be measured selectively. The polarity of the DNA molecule is selected, and the DNA molecule can be measured. It is possible to drive the same DNA molecule captured in the nanopore reversibly and unidirectionally, and to perform a sequence analysis in the same DNA molecule multiple times. Therefore, the accuracy of analyzing a base sequence can be improved. The DNA molecule is driven discontinuously. Therefore, detection can be performed at a high S/N by time-averaging electric signals. An electric circuit disposed in the nanopore can be cooled. Therefore, detection accuracy can be improved.

DESCRIPTION OF EMBODIMENTS

Figure 1:
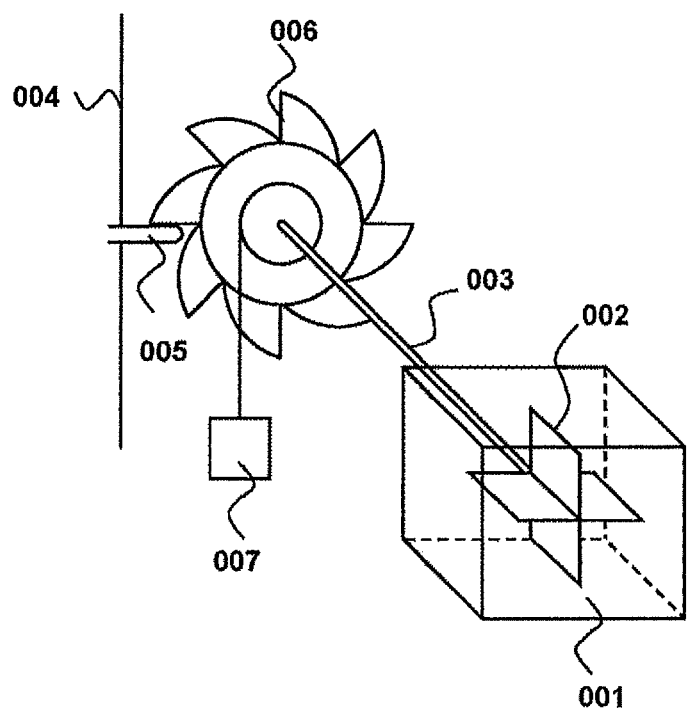
FIGS. 1a and 1b are diagrams illustrating a device for extracting unidirectional motion by introducing a temperature difference between molecules in Example 1.
Figure 1:
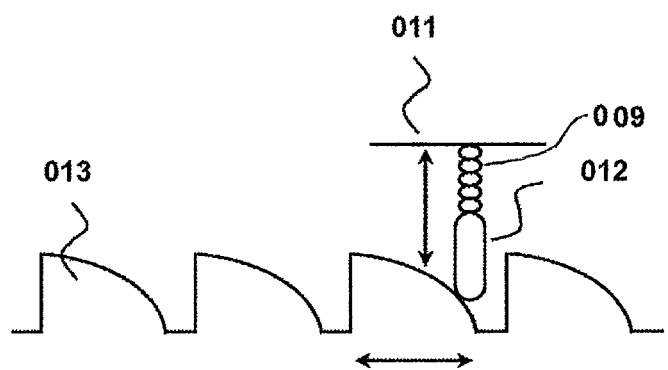

Examples of the present invention will be described.

Example 1

As a first Example of the present invention, a thermal ratchet device which is a method for moving a substance unidirectionally in a micro region, will be described with FIGS. 1a and 1b. This device includes a ratchet 006 having asymmetric teeth, an impeller 002, and a clasp 005 held on a wall 004. The ratchet 006 and the impeller 002 are connected to and fixed by an axis 003.

This impeller 002 is in a box 001 including a gas at a temperature T1. Therefore, a gas molecule at the temperature T1 collides with the impeller 002, and the impeller 002 receives a random force clockwise or counterclockwise from the gas molecule. The temperature of the wall 004 and the clasp 005 is represented by T2. A spring 009 is attached to the clasp 005. When the ratchet 006 tries to rotate clockwise, the clasp 005 retracts to the wall 004 left side and the ratchet 006 can rotate clockwise. When the ratchet 006 tries to rotate counterclockwise, the ratchet 006 stops at the clasp 005. In this system, it is known that unidirectional rotation does not occur as long as there is no difference between the temperature T1 of the impeller 002 and the temperature T2 of the wall 004 and the clasp 005. When T1>T2, the ratchet 006 can rotate clockwise and can pull up a load 008 outside. When T1<T2, the ratchet 006 can rotate counterclockwise. That is, the direction of the rotation is determined by a balance between thermal fluctuation motion of the rotation of the ratchet 006 and horizontal thermal fluctuation motion of the clasp 005. As described in the present Example, it is known in principle that unidirectional motion can be caused even in a micro region by introducing a temperature difference between the temperature T1 of the impeller 002 connected to the asymmetric ratchet 006 and the temperature T2 of the wall 004 and the clasp 005.

FIG. 1b illustrates a ratchet 013 (=rack) obtained by modifying the circular ratchet 006 in FIG. 1a into a linear shape. Thermal motion of the linear ratchet 013 in the left and right directions moves a clasp 012 upward. In order to move the clasp 012 upward, it is necessary to impart an energy E. This is equal to enhancing an energy of a spring internally existing in the clasp 012. When the ratchet 013 receives a horizontal kinetic energy and pushes the clasp 012, the clasp 012 retracts and the ratchet 013 moves to the right side. At this time, a probability at which the ratchet 012 receives energy is represented by [Mathematical Formula 1].

$$\exp\left(-\frac{\varepsilon}{kT_1}\right) \qquad \text{[Mathematical Formula 1]}$$

Here, k represents a Boltzmann constant. T1 represents the temperature of the ratchet 013. The temperature of the clasp 012 is represented by T2. A probability at which the clasp 012 retracts by itself is represented by [Mathematical Formula 2].

$$\exp\left(-\frac{\varepsilon}{kT_2}\right) \qquad \text{[Mathematical Formula 2]}$$

Therefore, when there is no load, the ratchet 013 can move unidirectionally as represented by [Mathematical Formula 3].

$$v = v_0 \left\{ \exp\left(-\frac{\varepsilon}{kT_1}\right) - \exp\left(-\frac{\varepsilon}{kT_2}\right) \right\}$$ [Mathematical Formula 3]

Example 2

Figure 2:
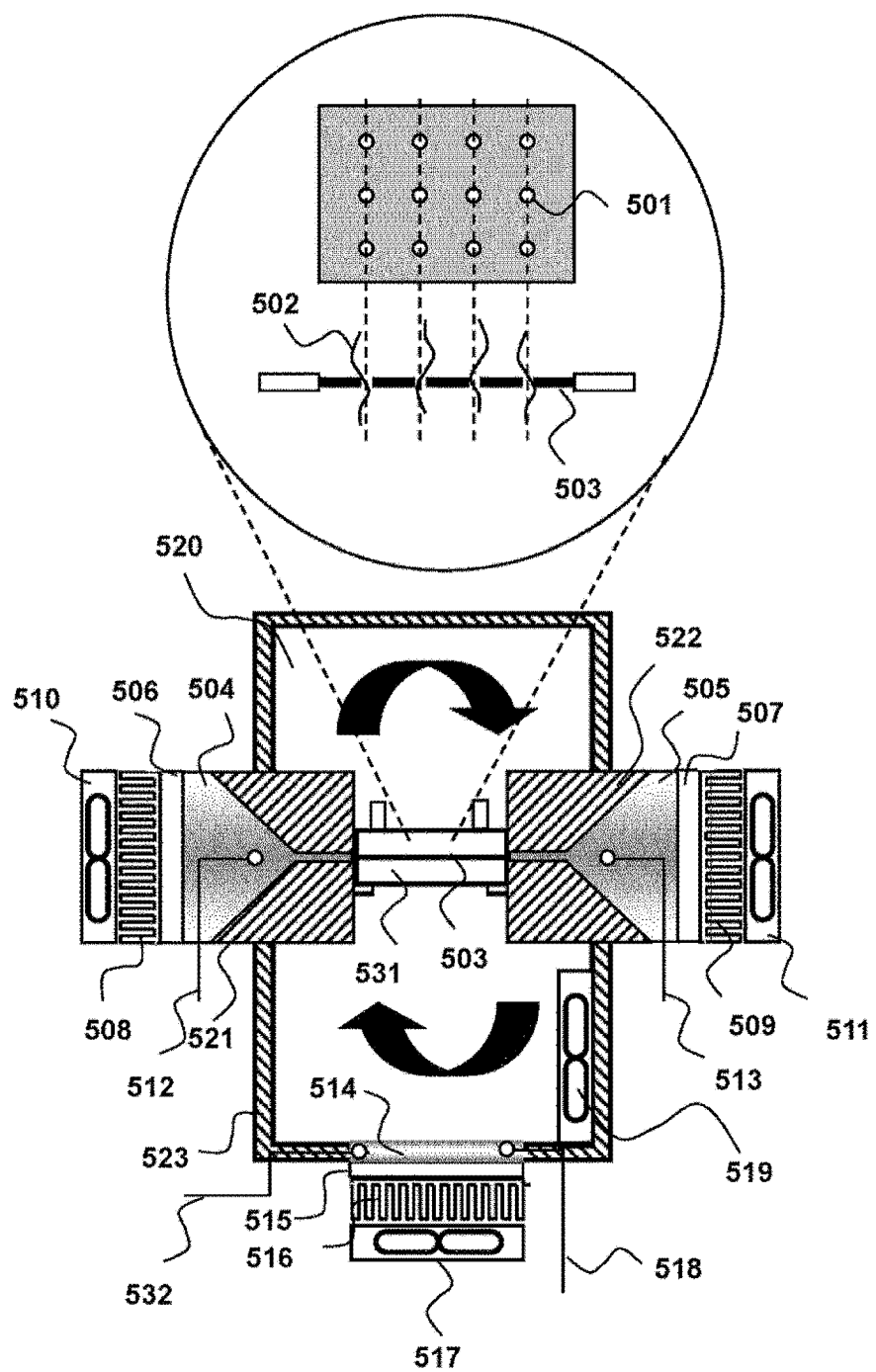
FIG. 2 is a diagram illustrating a device for analyzing a base sequence of a DNA single strand by introducing a temperature difference between molecules in Example 2.
Figure 3:
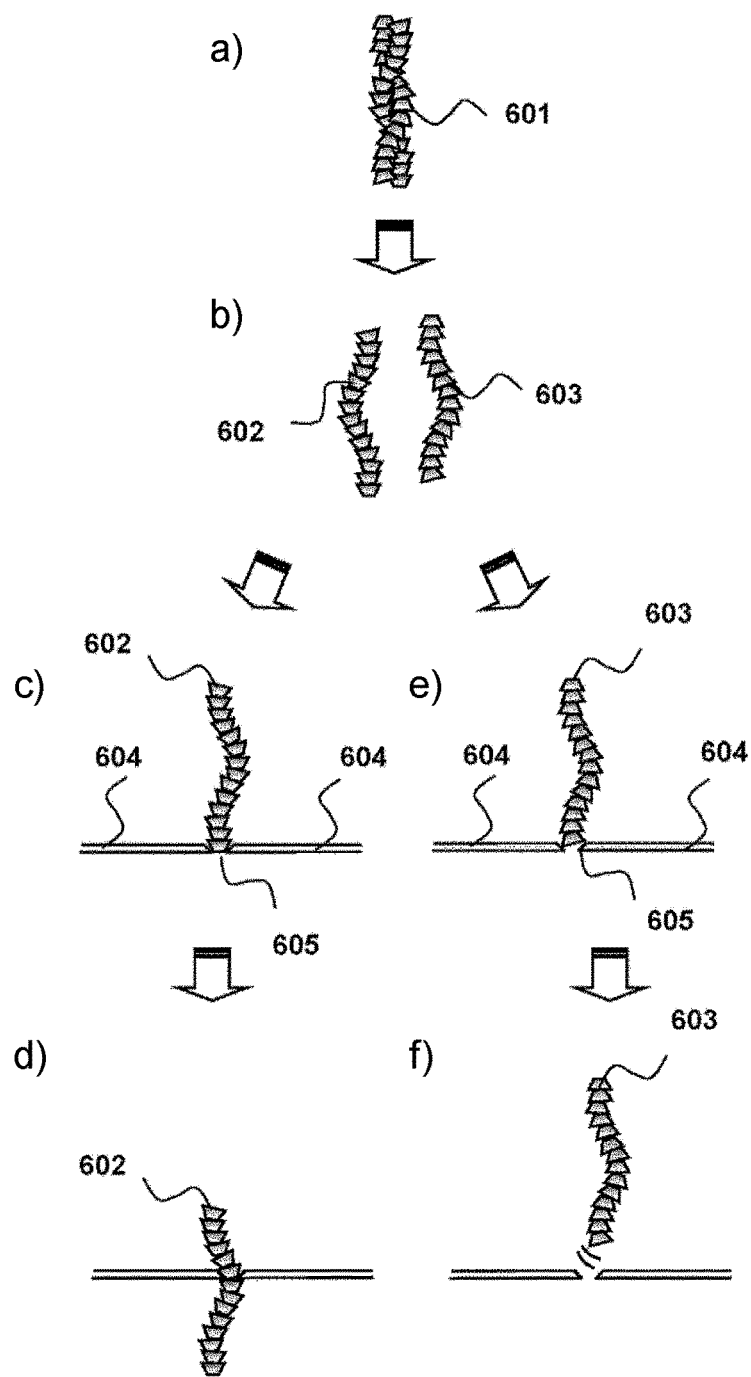
FIGS. 3a to 3f are diagrams illustrating a method for preparing a single stranded DNA from a double stranded DNA and selecting a polarity of the DNA molecule passing through a nanopore in Example 3.

As a second Example of the present invention, a structure of a device for driving a DNA molecule unidirectionally by introducing a temperature difference in a local micro region, controlling a driving speed, and decoding a base sequence of the DNA molecule, will be described with FIG. 2 hereinafter.

A thermostatic bath 520 heats an aluminum plate 514 with a Peltier element 515, and controls the temperature in the thermostatic bath 520 to T1 by heating the air in the thermostatic bath 520. Heating control by the Peltier element 515 is performed by feedback-controlling a temperature value from a temperature measuring resistor 518 disposed in the aluminum plate 514. More specifically, precise temperature control is performed by PID control. As concrete specifications of the thermostatic bath 520, a region of adjusting the temperature is from 0 to 100° C., an allowable temperature difference is ±0.5° C., and temperature stability is SD<0.06° C. (10 minutes). A thermal protector 532 is disposed in the thermostatic bath 520. When temperature runaway of 105° C. or higher occurs, supply of a voltage to the Peltier element 515 is cut off, and heating is stopped.

When the Peltier element 515 is driven, heat transfer occurs between the surface and the back surface of the Peltier element 515 due to a Seebeck effect, and a temperature difference occurs. When the temperature difference ΔT between the surface and the back surface satisfies ΔT=0, the Peltier element 515 can transfer a heat amount Qc at the highest efficiency. When the temperature difference occurs, a driving efficiency of the Peltier element 515 is lowered. Therefore, a fin 516 and a fan 517 are disposed on a Peltier surface in contact with the air outside in order to reduce the temperature difference. A fan in bath 519 is disposed in order to make the temperature distribution T1 of the air in the thermostatic bath 520 uniform. This makes it possible to circulate the air heated by the aluminum plate 514 in the thermostatic bath 520 and to make the temperature in bath T1 uniform. The thermostatic bath 520 is covered with a heat insulating material 523 in order to avoid change in the temperature due to inflow and outflow of heat from a surrounding environment.

A flow cell 531 is disposed in the thermostatic bath 520. A solution including a DNA molecule 502 is injected into the flow cell 531 via a septum, and is equilibrated at the temperature T1 in the thermostatic bath 520. A nanopore film 503 constituting a nanopore is stretched horizontally in the flow cell 531. The nanopore film 503 includes contact portions at both ends of the flow cell 531 outside, and these contact portions can be brought into contact with heat blocks 504 and 505. The heat blocks 504 and 505 can be cooled to the same temperature T2 by driven Peltier elements 506 and 507, respectively. Temperature measuring resistors 512 and 513 which are temperature sensors are embedded in the heat blocks 504 and 505, respectively. Temperature control is performed by PID control. The heat blocks 504 and 505 are equipped with heat insulating materials 521 and 522, respectively, in order to prevent heat transfer by direct contact between the temperature T2 of the heat blocks 504 and 505 and the temperature T1 in the thermostatic bath 520. Fins 508 and 509 and fans 510 and 511 are attached to the Peltier elements 506 and 507, respectively, in order to exhaust heat generated in the Peltier elements 506 and 507. The nanopore film 503 includes one or more nanopores 501. As described in detail in Examples below, the DNA molecule 502 in the flow cell 531 is in a form of a double strand when a sample is injected, but is heated to the temperature in bath T1 and is unwound into single strands. The DNA molecule unwound into single strands is guided to a nanopore 501 opening by an external electrode disposed in the flow cell 531. The temperature of each of a solution including the DNA molecule and the DNA molecule 502 is T1, and is controlled stably. The nanopore film 531 is cooled to the temperature T2 by the Peltier elements 506 and 507. This makes it possible to introduce a temperature difference between the DNA molecule 502 and the nanopore opening, and to realize the circumstances described in Example 1. Therefore, the DNA molecule 502 can be driven unidirectionally. By further setting the temperatures T1 and T2 to any values, it is possible to control a driving speed of the DNA molecule 502 represented by [Mathematical Formula 3] to any speed. The temperature range of T1 is from 30 to 100° C., more specifically from 60 to 95° C., still more specifically 94° C. Similarly, the temperature range of T2 is from 0 to 30° C., more specifically from 2 to 20° C., still more specifically 4° C. The driving speed of the DNA molecule 502 is from 0.03 to 3 μm/s, more specifically 0.3 μm/s. It is possible to analyze a base sequence of the DNA molecule 502 with resolution of one base by measuring a blockage current caused when the DNA molecule 502 passes through the nanopore film 503 or a tunneling current detected by a microelectrode disposed near the nanopore under these measuring conditions.

A conventional DNA sequencer requires an expensive optical system such as a CCD camera or an object lens, a driving unit using a motor, and an enzyme and a fluorescence reagent for performing a base extension reaction. However, the analysis device reported in the present Example does not require the optical system or the driving unit. The base extension is performed with an enzyme in a usual device. However, in the present Example, the role is played by the temperature difference introduced between the molecules and asymmetry of the DNA molecule, and therefore the enzyme is not required. It is not necessary to exchange solutions, and therefore the device can be compact. Therefore, it is possible to provide a DNA sequencer which is very simple, inexpensive, robust, and compact.

Example 3

As a third Example of the present invention, a method for making double stranded DNA passing through the nanopore into single stranded DNA will be described with FIGS. 3a to 3f hereinafter.

DNA the sequence of which is to be analyzed is extracted from blood, urine, saliva, biopsy, a cultivation cell, a tissue section, or the like. The DNA extracted and purified from these biological materials is not in a form of a single strand but in a form of a double strand. This is because complementary strands are bonded to each other in the DNA by forming a hydrogen bond, and the DNA turns into a form of a double strand and thereby minimizes free energy to be stabilized. In the double strand, single stranded DNA holding protein synthesis information is referred to as a sense strand, and the other single stranded DNA is referred to as an antisense strand.

When a base sequence of a DNA double strand is performed using a nanopore analysis method, two bases derived from a sense strand and an antisense are mixed in a distance 0.34 nm between molecules per base, and are wound around each other. Therefore, accuracy of the base sequence is largely reduced. Even when a graphene film which is thought to have the highest resolution at the present is used, effective spatial resolution is thought to be 0.35 nm. Therefore, it is extremely difficult to analyze a base sequence of a DNA molecule at high accuracy in a form of a double strand. Therefore, the DNA molecule introduced into the nanopore is required to be in a form of a single strand. In the present Example, a method for making this possible will be described.

In a), a double stranded DNA molecule 601 prepared by a usual method is floating in a solution.

In b), the solution in the thermostatic bath described in Example 2 is heated by temperature controlling by a Peltier element. The temperature of the solution including the double stranded DNA molecule 601 is thereby raised to a temperature Tm at which the double stranded DNA molecule 601 is unwound into single strands, and the double stranded DNA molecule 601 is separated into a sense DNA molecule 602 and an antisense DNA molecule 603 which are complementary single strands. Here, Tm is referred to as melting temperature, and a temperature of 90 to 95° C.

In c), the sense DNA molecule 602 is a polymer obtained by polymerizing four kinds of nucleotides. The chemical structures of the four kinds of nucleotides are very similar to each other. A DNA strand is formed by regularly stacking these nucleotides spirally. This DNA strand is characterized in that the DNA strand has an asymmetric form periodically because nucleotide molecules having almost the same structure are stacked. This asymmetric structure is not limited to a physical three-dimensional form, but may be a profile of an electrical interaction or a chemical interaction between molecules. The sense DNA molecule 602 having a saw shape and an asymmetric and periodic form performs electrophoresis due to an electric field applied to a solution, and is guided to a nanopore 605. This uses the characteristic that DNA is charged negative. The electrophoresis can be performed by applying a voltage to an external electrode disposed in each of upper and lower regions separated by a nanopore film 604 in a flow cell. In this state, the temperature of the nanopore 604 is not lowered and is the same temperature T1 as the solution. A spring mechanism is present near the nanopore 605. Therefore, the sense DNA molecule 602 cannot invade the nanopore 605, and performs a Brownian motion near the nanopore 605 due to an electric field.

In d), the temperature of the nanopore film 604 is lowered to T2 for the first time. This cooling is performed by a Peltier element connected to the outside. The temperature of the sense DNA molecule 602 is the same as the temperature T1 to which the solution in the flow cell has been heated. This makes it possible to introduce a temperature difference T1−T2 between the sense DNA molecule 602 and the nanopore film 604. The sense DNA molecule 602 has a saw shape having a periodic and asymmetric structure. Therefore, the sense DNA molecule 602 is driven downward by the introduced temperature difference T1−T2. This driving occurs for each base stepwise and discretely. This is largely different from conventional continuous motion of the sense DNA molecule 602 due to an electric field. This can be explained by the following. That is, an electric field gradient driving the electrophoresis is macro and a constant force not changing with time. Meanwhile, the driving force in the present Example is micro due to thermal fluctuation and changes with time. Only a force exceeding a threshold at a certain probability and having directivity contributes to advancing the sense DNA molecule 602. Many molecular fluctuations in the threshold do not contribute to final driving of the sense DNA molecule 602, and the sense DNA molecule 602 stays at a potential minimum position thereof in most cases. Therefore, it is possible to detect with high accuracy a blockage current or a tunneling current depending on a base by obtaining a time average of most parts which are at potential minimum. Here, a molar polarity of the sense DNA molecule 602 passing through the nanopore 605 is limited to a 5'→3' direction and a 3'→5' direction.

In e), the saw shape of the antisense DNA molecule 603 faces upward. In this state, the antisense DNA molecule 603 is guided to the nanopore 605 by electrophoresis. In this case, the temperature difference T1−T2 is introduced between the antisense DNA molecule 603 and the nanopore film 604. However, the antisense DNA molecule 603 is in contact with the nanopore film 604 while the saw shape of the antisense DNA molecule 603 is oriented upward. Therefore, a driving force derived from the temperature to the antisense DNA molecule 603 acts upward. Therefore, as illustrated in f), the antisense DNA molecule 603 cannot invade the nanopore 605. This is because the molar polarity of the antisense DNA molecule 603 disposed with respect to the nanopore 605 is different from the polarity of the sense DNA molecule 60 in c). When the polarity of a DNA molecule which can pass through the nanopore is the 5'→3' direction, a DNA molecule having a polarity of the 3'→5' direction cannot pass through the nanopore. Alternatively, when the polarity of the DNA molecule which can pass through the nanopore is the 3'→5 direction, a DNA molecule having a polarity of the 5'→3' direction cannot pass through the nanopore.

Therefore, in the present Example, the double stranded DNA can be unwound thermally, and only the single stranded DNA can be discriminated and selected, and can pass through the nanopore. This makes it possible to improve accuracy of analyzing abase sequence. In addition, it is possible to make the polarities of the single stranded DNA molecules have the same direction in passing through the nanopore.

Example 4

Figure 4:
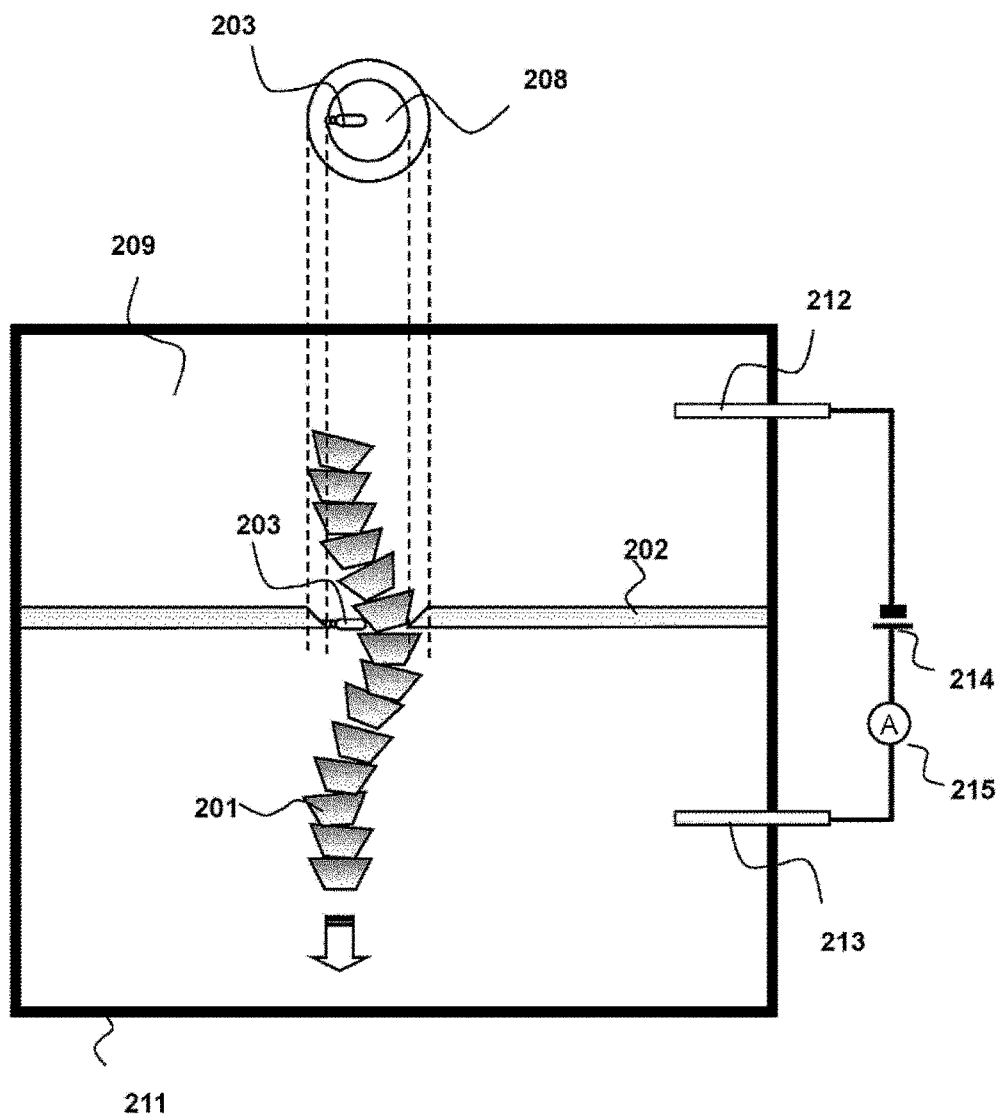
FIG. 4 is a diagram illustrating a method for analyzing a DNA base sequence by introducing a temperature difference between molecules and detecting a blockage current in Example 4.

As a fourth Example of the present invention, a nanopore measurement method and a device for decoding a base sequence of a DNA molecule by driving the DNA molecule unidirectionally by introducing a temperature difference in a micro region, will be described with FIG. 4 hereinafter.

A flow cell 211 is filled with a conductive solution including a DNA molecule 201. A nanopore film 202 separating the inside of the flow cell 211 into two portions sis and trans is present in the flow cell 211. A nanopore is formed in the nanopore film 202. Here, the diameter of the nanopore is appropriately 5 nm or less, more preferably 2 nm or less. The radius thereof is most preferably 1.2 nm. The thickness of the nanopore film is appropriately 1 nm or less, more preferably 0.5 nm or less. This nanopore can be formed by drilling using a focused electron beam, milling using a focused ion beam, reactive ion etching, or the like. Specific examples of a material forming the nanopore film 202 include graphene. Advantages in applying graphene for decoding a DNA base sequence are the following three points.

(1) Graphene has a thickness of one carbon atom, and has resolution to detect 0.34 nm which is a thickness of one nucleotide in DNA.

(2) The thermal conductivity of graphene is highest in the currently known substances. A value thereof is 5000 [W/m/K]. On the other hand, the thermal conductivity of water is 0.6. There is a difference of about four orders of magnitude as the order of thermal conductivity. Therefore, these substances have ideal characteristics in introducing a temperature difference in a micro region including both of the two.

(3) The Young's modulus of graphene is highest in the currently known substances. A value thereof is 1500 [GPa]. Therefore, a strong film which is not easily broken can be formed even if the film has only one layer.

The DNA molecule 201 is a polymer obtained by polymerizing four kinds of nucleotides. The chemical structures of the four kinds of nucleotides are very similar to each other. A DNA strand is formed by regularly stacking these nucleotides spirally. This DNA strand is characterized in that the DNA strand has an asymmetric form periodically because nucleotide molecules having almost the same structure are stacked. This asymmetric structure is not limited to a physical three-dimensional form, but may be a profile of an electrical interaction or a chemical interaction between molecules.

A spring mechanism 203 is disposed at an opening of the nanopore film 202. The spring mechanism 203 presses the DNA molecule 201 to the nanopore and holds the DNA molecule 201. The DNA molecule 201 has an asymmetric shape. Therefore, the spring mechanism 203 presses a portion of the DNA molecule 201 having a small diameter. Specific candidates of the spring mechanism 203 include a polymer such as nanotube or nanowire. In addition, the graphene film itself also acts as the spring mechanism 203. In addition, a biological polymer such as actin filament, microtube, or a DNA single strand can be used as the spring mechanism 203.

The DNA molecule 201 is electrically charged negative. Therefore, the DNA molecule 201 can be guided to the vicinity of the nanopore opening and can be brought into contact with the nanopore by applying a voltage to the solution by external electrodes 212 and 213. The spring mechanism 203 is disposed at the nanopore opening. The DNA molecule 201 cannot invade the nanopore opening and stays around the nanopore opening until the spring receives an energy ε required for contracting itself from a surrounding environment.

The inside of the flow cell 211 is disposed in a thermostatic bath adjusted to the temperature T1. Therefore, the temperatures of a DNA solution in the flow cell 211 and the DNA molecule 201 in the solution are also T1. Moving of the DNA molecule 201 to the vicinity of the nanopore opening can be detected by decrease in a blockage current. After the decrease in the blockage current is confirmed, the nanopore film 202 is cooled to the temperature T2 using a Peltier element from the outside of the flow cell 211 by the method described in Example 2. Here, T1>T2. The DNA molecule 201 performs a Brownian motion reflecting the temperature T1 in the solution. Meanwhile, the spring mechanism 203 performs a Brownian motion reflecting the temperature T2 of the nanopore film 202. When T1>T2, the DNA molecule 203 stochastically acquires an energy ε required for contracting the spring mechanism 203 in giving energy to or receiving energy from the heat bath. At this time, the DNA molecule 201 imparts the energy ε to the spring mechanism 203 and contracts the spring mechanism 203. As a result, the DNA molecule 201 pushes up the spring mechanism 203, and moves downward by one base. Thereafter, the DNA molecule 201 repeats the above-described motion, and thereby passes through the nanopore. Movement by one base is generated stochastically, discontinuously, and discretely. It is possible to control the passing speed of the DNA molecule arbitrarily by tuning the temperatures T1 and T2 and the energy ε (=hardness of spring) required for pushing up the spring. When the DNA molecule passes too fast, it is possible to reduce the passing speed of the DNA molecule by tuning. When the temperature T1>T2, the passing speed of the DNA molecule 203 in the nanopore is represented by [Mathematical Formula 4].

$$v = v_0 \left\{ \exp\left(-\frac{\varepsilon}{kT_1}\right) - \exp\left(-\frac{\varepsilon}{kT_2}\right) \right\} \quad \text{[Mathematical Formula 4]}$$

When each base of the DNA molecule 201 passes through the nanopore successively, an effective area of the nanopore through which ions can pass changes. At this time, a voltage is applied to the external electrodes 212 and 213 in advance. Therefore, it is possible to detect a blockage current which is an ion current passing through gaps between the nanopore and the DNA molecule 201. Therefore, the spring mechanism 203 stays in a state holding a small diameter of the DNA molecule 201 in most of the moving time. It is possible to detect this blockage current by an ammeter 215 and read a sequence of the DNA molecule 201. Advantages of a nanopore base sequence analysis by a thermal ratchet mechanism will be described below.

(1) By introducing a temperature difference between molecules, the passing speed of a DNA molecule in a nanopore can be controlled arbitrarily. More specifically, the passing speed of the DNA molecule can be reduced.

(2) The DNA molecule is driven successively and discontinuously. Therefore, it is possible to detect a DNA base sequence at a higher S/N by time-averaging electric signals detecting a state of a nucleotide. The DNA passes successively and discontinuously in a unit of a nucleotide, and the DNA molecule moves by one base. Thereafter, the DNA molecule stops motion at a potential minimum in one base. When one base is held by the thermal ratchet mechanism, the blockage current fluctuates, but an average thereof is a current value at the potential minimum in one base. This makes it possible to perform measurement stably by taking a time average in a sufficiently long time even when a feeble blockage current is detected.

(3) Double stranded DNA is unwound thermally, and only single stranded DNA is measured selectively. In double stranded DNA, single stranded DNAs are wound around each other complementarily and spirally. Therefore, it is necessary to examine whether a signal change obtained from a blockage current or a tunneling current is derived from the double stranded DNA or the single stranded DNA, and accuracy of the analysis is largely reduced. On the other hand, in the present Example, it is possible to easily guide the single stranded DNA to a nanopore by heating a solution 209 in the flow cell 211 to a temperature (melting temperature) at which the double stranded DNA is unwound.

(4) The polarity of a single stranded DNA molecule with respect to a nanopore film can be discriminated, selected, and measured. More specifically, it is possible to analyze a base sequence by selectively discriminating and selecting a polarity from a 5' terminal to a 3' terminal or a molar polarity opposite thereto.

It is also possible to reduce the passing speed of the DNA molecule 201 due to the external electric field only by introducing the spring mechanism 203 without introducing the temperature difference T1-T2.

Example 5

Figure 5:
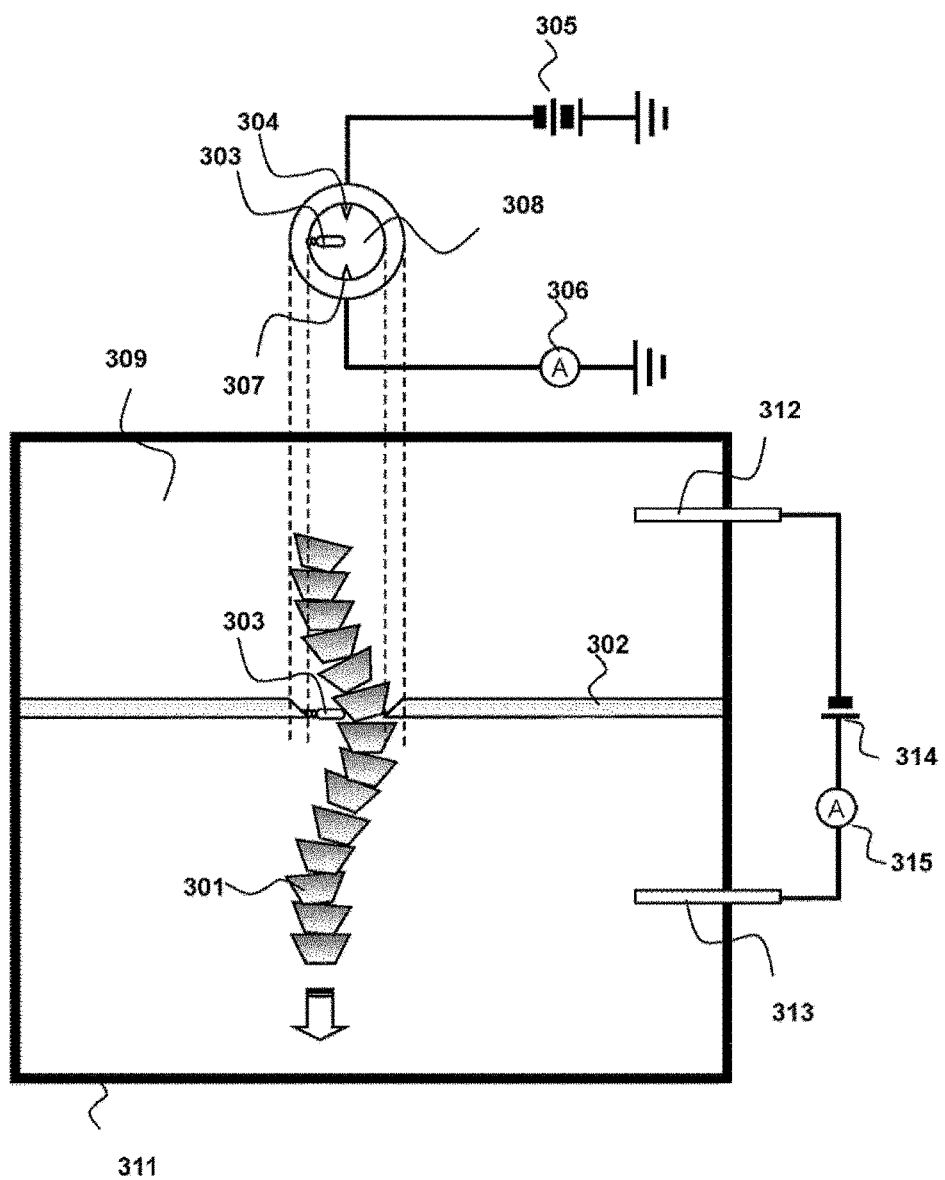
FIG. 5 is a diagram illustrating a method for analyzing a DNA base sequence by introducing a temperature difference between molecules and detecting a tunneling current in Example 5.

As a fifth Example of the present invention, a nanopore measurement method and a device for decoding a base sequence of a DNA molecule by driving the DNA molecule unidirectionally by introducing a temperature difference in a micro region, will be described with FIG. 5 hereinafter. In the fourth Example, a blockage current is used for reading the base sequence. However, in the present Example, a tunneling current is used.

A DNA molecule 301 is electrically charged negative. Therefore, the DNA molecule 301 can be guided to the vicinity of a nanopore opening and can be brought into contact with the nanopore by applying a voltage to a solution by external electrodes 312 and 313. A spring mechanism 303 is disposed at the nanopore opening. The DNA molecule 301 cannot invade the nanopore opening and stays around the nanopore opening until the spring receives an energy ε required for contracting itself from a surrounding environment.

A flow cell 311 is disposed in a thermostatic bath adjusted to the temperature T1. Therefore, the temperature of a DNA solution in the flow cell is also T1, and the temperature in the DNA molecule 301 in the solution is also T1. Moving of the DNA molecule 301 to the vicinity of the nanopore opening can be detected by decrease in the blockage current. After the decrease in the blockage current is confirmed, the nanopore film 302 is cooled to the temperature T2 using a Peltier element from the outside of the flow cell 311 by the method described in Example 2. Here, T1>T2. By cooling, the DNA molecule 301 starts to move into the nanopore. At this time, the tunneling current is detected by microelectrodes 304 and 307. After detection of the tunneling current is confirmed, application of a potential to the external electrodes 312 and 313 is stopped. This makes it possible to remove a force of electrophoresis and to control the motion of the DNA molecule 311 only by the temperature difference T2-T1. This makes it possible to control the motion of the DNA molecule 301 at higher accuracy in an environment in which an influence by an external electric field is eliminated. Hereinafter, advantages of the present Example will be summarized.

(1) It is possible to eliminate an influence by an external electric field used for electrophoresis and to control unidirectional motion of a DNA molecule purely with a driving force derived from a temperature difference.

(2) Parallelization in nanopore measurement is possible. A blockage current measures an ion current passing through a nanopore. Therefore, even when a plurality of nanopores is disposed on a nanopore film, the blockage current can measure only the total of the ion currents passing through the nanopores. Therefore, parallelization in nanopore measurement is difficult. On the other hand, in a method using a tunneling current, each circuit for detecting a tunneling current of each of the plurality of nanopores disposed is disposed. Therefore, parallelization processing in nanopore measurement is possible.

(3) An electric circuit disposed on a nanopore film is cooled to the temperature T2 by a Peltier element outside a flow cell. Generally, a noise in an electric circuit is roughly classified into a thermal noise and a shot noise. The former is a random noise caused by heat of electrons. The latter noise is caused because electrons flowing in an element are discrete, and cannot generate a continuous and steady flow. Both of these noises can be reduced by cooling the element in the electric circuit. A tunneling current in nanopore measurement is extremely feeble. Therefore, cooling the electric circuit is effective for improving a signal noise ratio of the tunneling current.

The temperature difference T2-T1 can be controlled arbitrarily from the outside. Therefore, a speed of the DNA molecule 301 passing through a nanopore can be also controlled arbitrarily. A material of the spring mechanism 303 can be selected. Therefore, by adjusting these parameters, it is possible to set the passing speed of the DNA molecule 301 arbitrarily. It is also possible to reduce the passing speed of the DNA molecule 301 due to the external electric field only by introducing the spring mechanism 303 without introducing the temperature difference T1-T2.

Example 6

Figure 6:
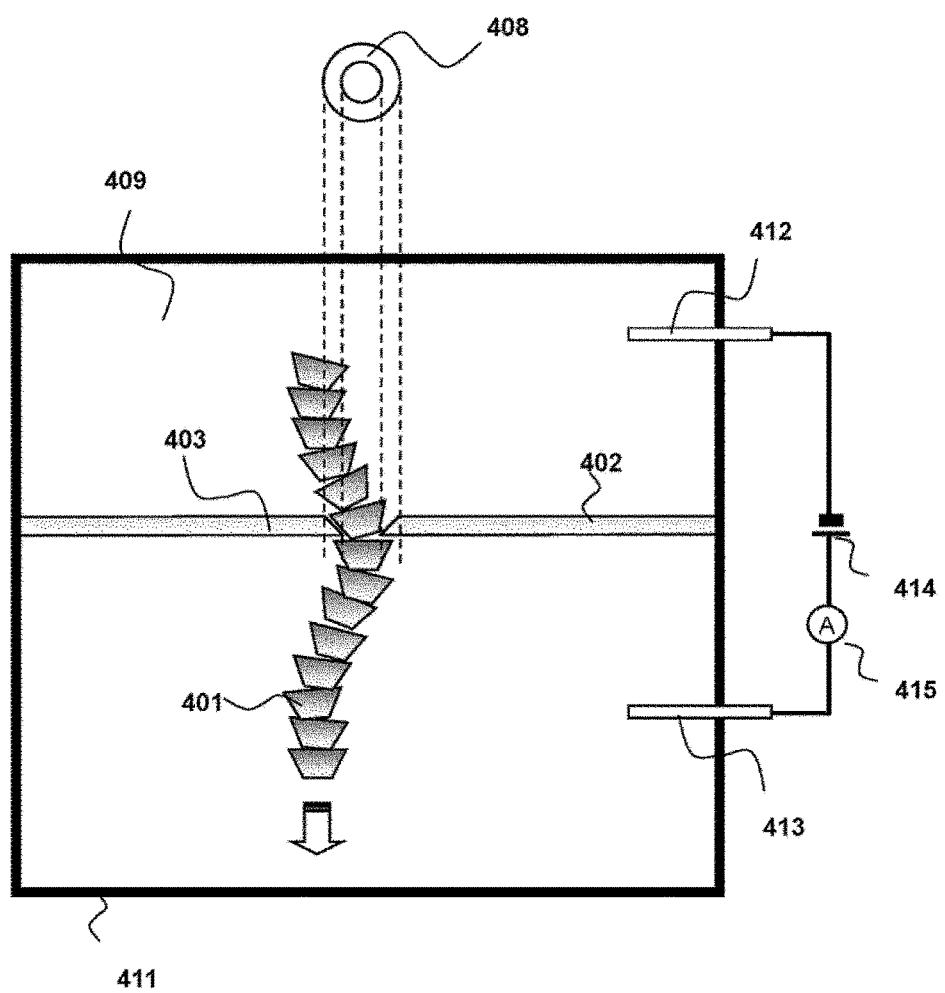
FIG. 6 is a diagram illustrating a method for analyzing a DNA base sequence by introducing a temperature difference between molecules and including a spring function in a nanopore film in Example 6.

As a sixth Example of the present invention, a method and a device for decoding a base sequence of a DNA molecule by not holding a spring mechanism but driving the DNA molecule unidirectionally, will be described with FIG. 6 hereinafter.

DNA 401 does not particularly hold a spring mechanism in a nanopore film 403. The nanopore film 403 itself internally includes a spring mechanism sufficiently. Therefore, unidirectional motion of a DNA molecule due to a temperature difference can be caused without particularly introducing a spring mechanism. This brings about the following advantages. That is, in the methods and devices described in Examples 4 and 5, it is not necessary to add a particular spring mechanism, and mass production can be performed easily and inexpensively.

Example 7

Figure 7:
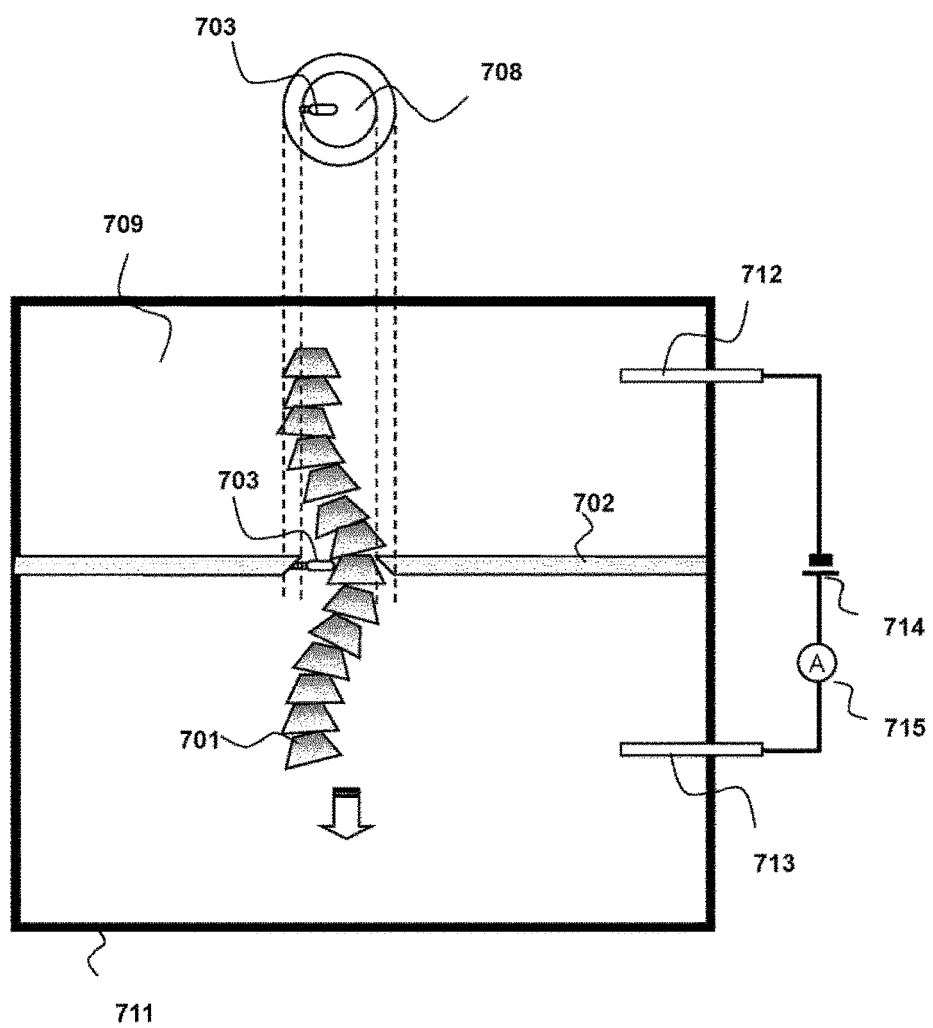
FIG. 7 is a diagram illustrating a method for controlling a speed of a DNA molecule passing through a nanopore by making an external electric field compete with a driving force caused by a temperature difference between molecules in Example 7.

As a seventh Example of the present invention, a method and a device for reducing a passing speed of a DNA molecule when an influence to make a DNA molecule pass through a nanopore by a force of electrophoresis is strong, will be described with FIG. 7 hereinafter.

Generally, a DNA molecule 701 moves in a nanopore at 100 um/sec by applying a voltage to external electrodes 712 and 713 in a flow cell. On the other hand, it is necessary to reduce the passing speed of DNA to 0.3 um/sec in order to perform nanopore measurement of the DNA molecule with resolution in a unit of a nucleotide.

In the present Example, a nanopore film 702 is cooled to T2 in advance in order to solve this problem. The temperature of a solution in a flow cell 709 is T1, and T1>T2.

The single stranded DNA molecule 701 is guided to the vicinity of a nanopore while the saw shape faces upward with respect to the nanopore film. Without an external electric field, it is possible to impart a driving force derived from a Brownian motion to the DNA molecule 702 by cooling the nanopore film 702 to T2. More specifically, it is possible to move the DNA molecule 702 above the nanopore film. With an external electric field, a substantial moving speed of a DNA molecule=a moving speed by the external electric field−a speed by introducing a temperature difference. Therefore, also in measuring a blockage current, it is possible to control and reduce a speed of the DNA molecule 702 passing through a nanopore by applying a temperature driving force competing with an external electric field force.

Example 8

As an eighth Example of the present invention, a structure of a device for reversibly driving a DNA molecule in both of the upper and lower directions by introducing a temperature difference in a local micro region, controlling a driving speed, and decoding a base sequence of a DNA molecule, will be described with FIG. 8 hereinafter. In Example 2, the temperature of a solution held by a flow cell is controlled by a thermostatic bath via an air layer. This is for maintaining the temperature of the solution in a steady state. In the present Example, a structure of a device for inverting the temperature T1 of a solution and the temperature T2 of a nanopore film will be described.

Figure 8:
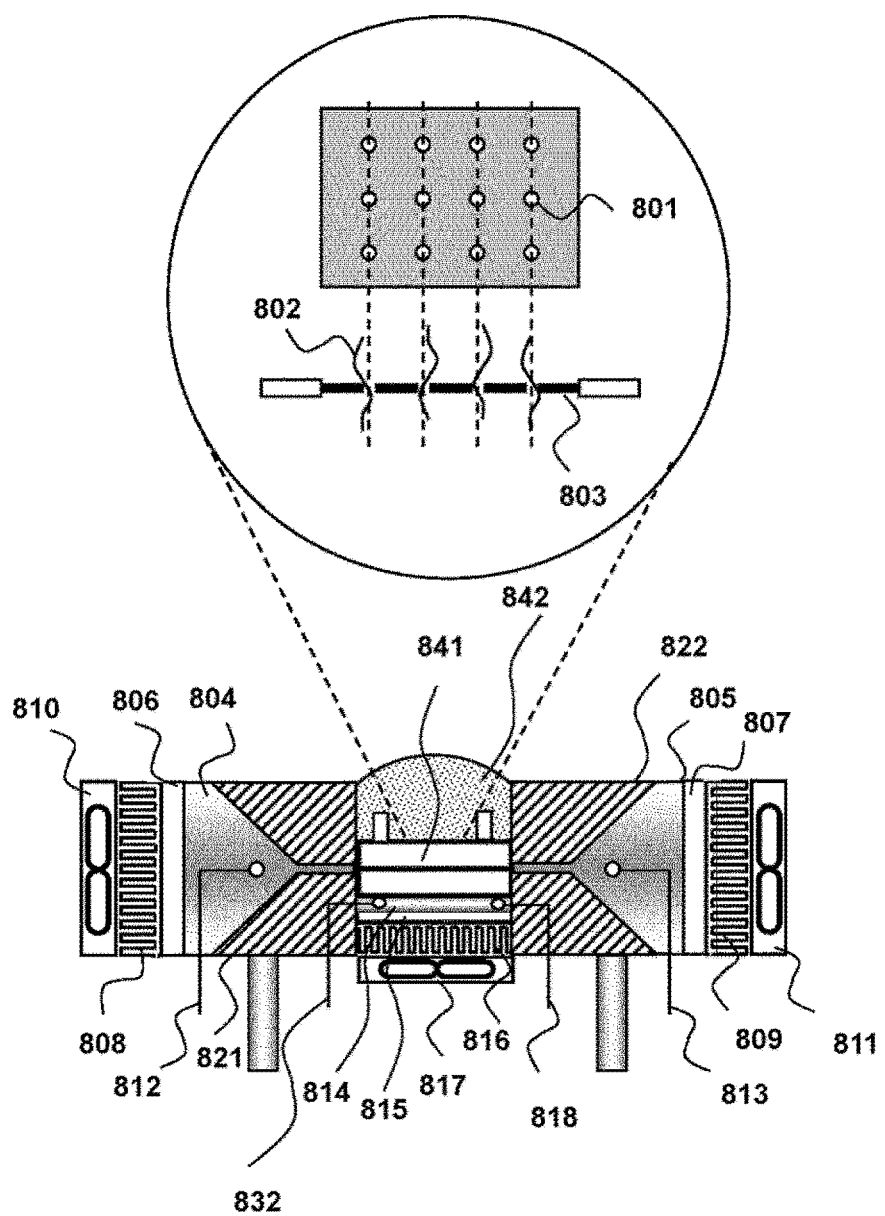
FIG. 8 is a diagram illustrating a device for analyzing a base sequence of a DNA single strand by inverting a temperature difference between molecules at a high speed in Example 8.

A temperature control device illustrated in FIG. 8 can control the temperature T1 of the solution in a flow cell 841 and the temperature T2 of the nanopore film independently. The temperature of the solution in the flow cell 841 disposed in the temperature control device is controlled to T1 by heating a heat block 814 by a Peltier element 815. Heating control by the Peltier element 815 is performed by feedback-controlling a temperature value from a temperature measuring resistor 818 disposed in the heat block 814. More specifically, precise temperature control is performed by PID control. As concrete specifications of the temperature control device, a region of adjusting the temperature is from 0 to 100° C., an allowable temperature difference is ±0.5° C., and temperature stability is SD<0.06° C. (10 minutes). A thermal protector 832 is disposed in the heat block 814. When temperature runaway of 105° C. or higher occurs, supply of a voltage to the Peltier element 815 is cut off, and heating is stopped.

When the Peltier element 815 is driven, heat transfer occurs between the surface and the back surface of the Peltier element 815 due to a Seebeck effect, and a temperature difference occurs. When the temperature difference $\Delta T$ between the surface and the back surface satisfies $\Delta T=0$, the Peltier element 815 can transfer a heat amount Qc at the highest efficiency. When the temperature difference occurs, a driving efficiency of the Peltier element 815 is lowered. Therefore, a fin 816 and a fan 817 are disposed on a Peltier surface in contact with the air outside in order to reduce the temperature difference. A cover 842 enhances adhesion between a flow cell 841 and the heat block 814, and improves heat transfer. The cover 842 also thermally insulates the flow cell 841 from an external environment.

A solution including a DNA molecule 802 is injected into the flow cell 841 disposed on the heat block 814 via a septum, and is equilibrated at the temperature T1. A nanopore film 803 constituting a nanopore is stretched horizontally in the flow cell 841. The nanopore film 803 includes contact portions at both ends of the flow cell 841 outside, and these contact portions can be brought into contact with heat blocks 804 and 805. The heat blocks 804 and 805 can be cooled to the same temperature T2 by driven Peltier elements 806 and 807, respectively. Temperature measuring resistors 812 and 813 which are temperature sensors are embedded in the heat blocks 804 and 805, respectively. Temperature control is performed by PID control. The heat blocks 804 and 805 are equipped with heat insulating materials 821 and 822, respectively, in order to prevent heat transfer by direct contact between the temperature T2 of the heat blocks 804 and 805 and the temperature T1 in the solution. Fins 808 and 809 and fans 810 and 811 are attached to the Peltier elements 806 and 807, respectively, in order to exhaust heat generated in the Peltier elements 806 and 807. The nanopore film 803 includes one or more nanopores 801. As described in Examples 3, the DNA 802 in the flow cell 841 is in a form of a double strand when a sample is injected, but is heated to the temperature T1 and is unwound into single strands. The DNA molecule unwound into single strands is guided to a nanopore opening by an external electrode disposed in the flow cell. The temperature of each of a solution including DNA and the DNA molecule 802 is T1, and is controlled stably. The nanopore film 803 is cooled to the temperature T2 by the Peltier elements 806 and 807. This makes it possible to introduce a temperature difference between the DNA molecule 802 and the nanopore opening, and to realize the circumstances described in Example 1. Therefore, the DNA molecule 802 can be driven unidirectionally.

The device described in the present Example can invert the temperature T1 of a solution in the flow cell 841 and the temperature of the nanopore film 803 reversibly at a high speed. Specifically, the ramp rate of the solution is 5° C./sec in heating and 2.5° C./sec in cooling. The ramp rate of the nanopore film is 100° C./sec in heating and 50° C./sec in cooling. This is explained by the fact that the thermal capacity of the nanopore is ½₀ or less as compared with that of a flow chip 841.

Example 9

Figure 9:
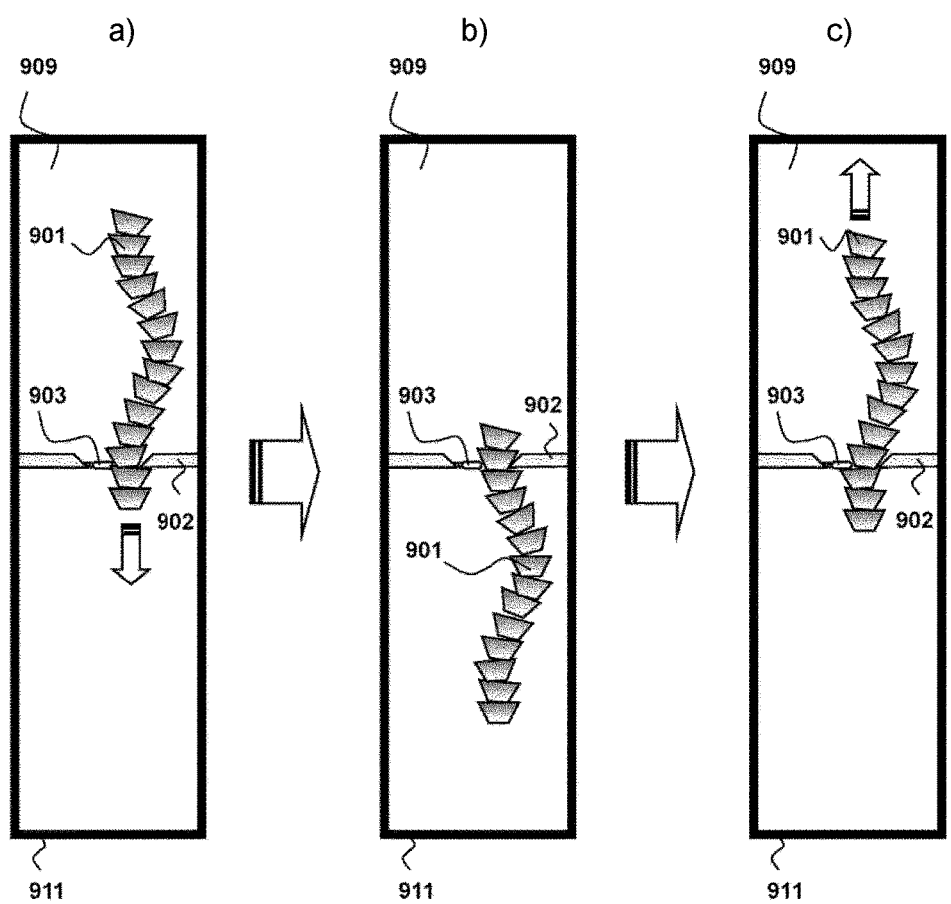
FIGS. 9a to 9c are diagrams illustrating a method for analyzing a base sequence of a DNA single strand by inverting a temperature difference between molecules at a high speed in Example 9.

As a ninth Example of the present invention, a method for reversibly driving the same single stranded DNA captured in a nanopore using the temperature control device described in FIG. 8, and analyzing a base sequence multiple times, will be described with FIGS. 9a to 9c hereinafter.

Generally, in order to raise accuracy of information of a base sequence, analysis results of a plurality of DNA fragments are superimposed on each other on a computer multiple times. More specifically, the human genome having a 3G base information amount empirically requires ten times more redundancy for producing reliable data. That is, a sample having a minimum necessary information amount is required in an amount of ten times. However, in a clinical field, it is often difficult to collect a sufficient amount of sample. In a method targeting measurement of one molecule DNA, a long base length can be read advantageously, but measurement accuracy of a base sequence in one measurement is 80-85%, which is disadvantageously very low. Meanwhile, public required accuracy of a base sequence of the human genome is 99.99% or more. Therefore, it is an important object to raise measurement accuracy in the one molecule measurement method. As for this object, the present Example proposes a method for repeatedly reading information of a base sequence reversibly in the same molecule.

In a) to b), a single stranded DNA 901 moves successively downward in a nanopore. A temperature 909 of a solution is T1 and the temperature of the single stranded DNA 901 is similarly T1. A nanopore film 902 is cooled, and the temperature thereof is T2. Here, T1>T2. By a local temperature difference T2−T1 introduced between the single stranded DNA 901 and the nanopore film 902, each base of the single stranded DNA 901 having a periodic and asymmetric structure moves downward successively and continuously. By measuring a blockage current or a tunneling current during moving, it is possible to read a base sequence of the single stranded DNA 901.

With respect to the DNA molecule in the state b), the temperature T1 in the solution is cooled to T2, and the temperature T2 in the nanopore film is heated to T1. The single stranded DNA 901 thereby moves upward as illustrated in b) to c). By repeating an operation a)→b)→dc) arbitrary times, it is possible to improve information of a base sequence of the single stranded DNA 901. It is thereby possible to measure a minute amount of sample in a clinical field inexpensively at high accuracy.

Example 10

Figure 10:
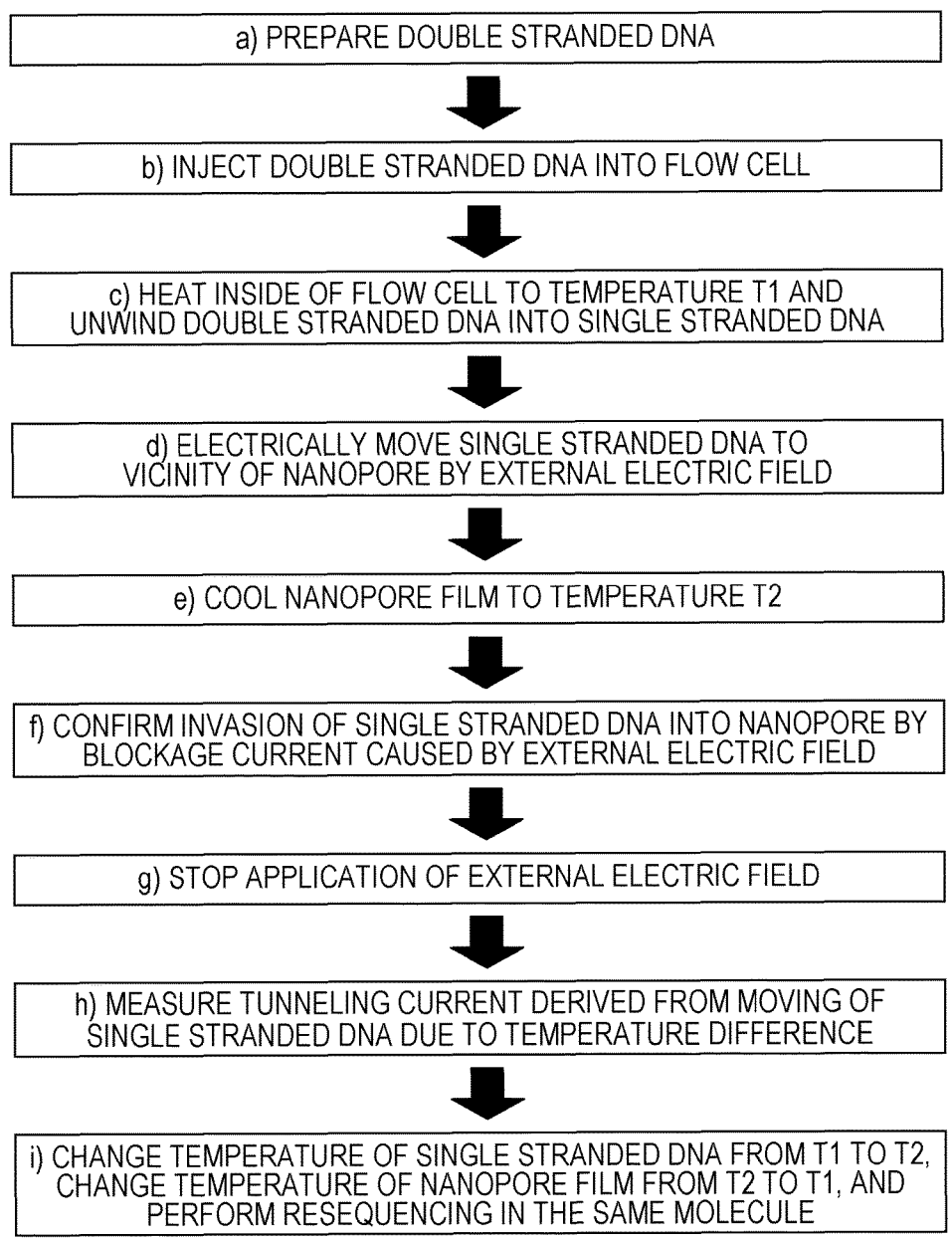
FIG. 10 is a diagram illustrating a flowchart of a method for analyzing a base sequence by introducing a temperature difference between molecules in Example 10.

As a tenth Example of the present invention, a representative work flow of a nanopore sequencing method using a temperature difference between molecules will be described with FIG. 10 hereinafter.

The representative work flow is as follows.

(a) Prepare a stranded DNA. (b) Inject double stranded DNA into a flow cell. (c) Heat inside of the flow cell to the temperature T1 and unwind double stranded DNA into single stranded DNA (d) Electrically move the single stranded DNA to the vicinity of a nanopore by an external electric field. (e) Cool a nanopore film to the temperature T2. (f) Confirm invasion of the single stranded DNA into the nanopore by a blockage current caused by an external electric field. (g) Stop application of the external electric field. (h) Measure a tunneling current derived from moving of the single stranded DNA due to a temperature difference. (i) Change the temperature of single stranded DNA from T1 to T2, change the temperature of the nanopore film from T2 to T1, and perform resequencing in the same molecule. However, this work flow is just an example, and an application method in the present invention is not limited to this work flow.

REFERENCE SIGNS LIST 001 box
002 impeller
006, 013 ratchet
004, 011 wall
005, 012 clasp
007 load
003 axis
520 thermostatic bath
515, 506, 507, 815, 806, 807 Peltier element
514 aluminum plate
532, 832 thermal protector
516, 508, 509, 816, 808, 809 fin
517, 510, 511, 817, 810, 811 fan
518, 512, 513, 818, 812, 813 temperature measuring resistor
531, 211, 709, 841 flow cell
502, 601 double stranded DNA
602, 201, 301, 701, 802, 901 single stranded sense DNA molecule
603 single stranded antisense DNA molecule
504, 505, 814, 804, 805 heat block
503, 604, 302, 403, 702, 803 nanopore film
501, 605, 202, 902 nanopore
212, 213, 312, 313, 712, 713 external electrode
304, 307 microelectrode
203, 303 spring mechanism
215 ammeter
209 solution
842 cover
821, 822 Heat insulating material

The invention claimed is:

1. An analysis device including a container holding a solution containing DNA or RNA, comprising:
a film having a nanopore, configured to separate the container into two regions;
an electrode configured to apply a voltage to the solution;
a first Peltier device to control the temperature of the solution to a first temperature;
a second Peltier device coupled with the film to control the temperature of the film to a second temperature which is different from the first temperature; and a current detector to detect a current of the nanopore as the DNA or RNA passes through the nanopore,
wherein the nanopore includes a spring mechanism to control passing of the DNA or RNA through the nanopore, and
wherein the spring mechanism comprises an actin filament.

2. The analysis device according to claim 1, wherein the current detector is configured to detect the current as an asymmetric and periodic DNA passes through the nanopore.

3. The analysis device according to claim 1, wherein the first Peltier device is configured to heat the solution to the first temperature and the second Peltier device is configured to cool the second temperature of the film to be lower than the first temperature of the solution.

4. The analysis device according to claim 1, wherein the first temperature of the solution is higher than the second temperature of the film.

5. The analysis device according to claim 1, wherein each of the first Peltier device and the second Peltier device includes a Peltier element, a fin, and a fan.

6. The analysis device according to claim 1, wherein the second Peltier device includes a heat insulating material configured to prevent heat transfer in the container.

7. The analysis device according to claim 1, wherein the container is surrounded by a heat insulating material.

8. The analysis device according to claim 1, comprising a container holding a solution containing the DNA or RNA.

9. The analysis device according to claim 1, wherein the film includes one or more outside contact portions to make contact with the second Peltier device.

10. An analysis method for decoding a base sequence of DNA,
separating a container into two regions by a film having a nanopore, one of the two regions holding a solution including DNA;
adjusting a temperature of the solution including the DNA to a first temperature using a first Peltier device:
adjusting a temperature of the film to a second temperature which is different from the first temperature using a second Peltier device coupled with the film:
guiding a DNA molecule of the DNA solution to the nanopore by applying a voltage inside the container;
controlling movement of the DNA molecule through the nanopore using a spring mechanism included in the nanopore, wherein the spring mechanism comprises an actin filament; and
detecting a blockage current of the nanopore or a tunneling current during the movement of the DNA molecule in the nanopore.

11. The analysis method according to claim 10, wherein controlling movement of the DNA molecule in the nanopore comprises controlling a passing speed of the DNA molecule passing through the nanopore.

12. The analysis method according to claim 10, wherein adjusting the temperature of the solution including the DNA comprises heating the solution to the first temperature and adjusting the temperature of the film comprises cooling the second temperature of the film to be lower than the first temperature of the solution.

13. The analysis method according to claim 10, wherein the first temperature of the solution including the DNA is higher than the second temperature of the film.

14. The analysis method according to claim 10, further comprising heat insulating the container to prevent heat transfer with external surrounding.

15. The analysis method according to claim 10, wherein a graphene film forms a nanopore membrane as the nanopore.

16. The analysis method according to claim 10, wherein the detecting comprises detecting the blockage current of the nanopore using an ammeter during the movement of the DNA molecule in the nanopore or detecting the tunneling current of the nanopore using microelectrodes during the movement of the DNA molecule in the nanopore.

17. The analysis device according to claim 1, wherein a graphene film forms a nanopore membrane as the nanopore.

18. The analysis device according to claim 1, wherein the current detector comprises an ammeter to detect a blockage current of the nanopore or microelectrodes to detect a tunneling current as the DNA passes through the nanopore.

* * * * *